(12) United States Patent
Quay et al.

(10) Patent No.: US 7,329,725 B1
(45) Date of Patent: Feb. 12, 2008

(54) PHAGE DISPLAYED TRP CAGE LIGANDS

(75) Inventors: Steven C. Quay, Edmonds, WA (US); Douglas L. Badders, Seattle, WA (US); Richard E. Herman, Redmond, WA (US); Michael E. Houston, Jr., Sammamish, WA (US); Paul Hickok Johnson, Snohomish, WA (US)

(73) Assignee: Nastech Pharmaceutical Company Inc., Bothell, WA (US)

( * ) Notice: Subject to any disclaimer, the term of this patent is extended or adjusted under 35 U.S.C. 154(b) by 75 days.

(21) Appl. No.: 10/976,942

(22) Filed: Oct. 29, 2004

Related U.S. Application Data

(60) Provisional application No. 60/515,533, filed on Oct. 29, 2003.

(51) Int. Cl.
- A61K 38/00 (2006.01)
- A61K 38/26 (2006.01)
- C12Q 1/68 (2006.01)
- C12N 7/00 (2006.01)
- C12N 15/00 (2006.01)

(52) U.S. Cl. .................. 530/326; 530/308; 435/6; 435/235.1; 435/320.1

(58) Field of Classification Search ........... 530/326, 530/308; 435/6, 235.1, 320.1
See application file for complete search history.

(56) References Cited

U.S. PATENT DOCUMENTS

| | | | |
|---|---|---|---|
| 5,407,911 A | 4/1995 | Yamamoto et al. | |
| 5,738,996 A | 4/1998 | Hodges et al. | |
| 5,824,483 A | 10/1998 | Houston, Jr. et al. | |
| 5,837,500 A | 11/1998 | Ladner et al. | |
| 5,864,009 A | 1/1999 | Vlasuk et al. | |
| 5,969,108 A * | 10/1999 | McCafferty et al. | 530/387.3 |
| 6,492,138 B1 | 12/2002 | McGlade et al. | |
| 6,746,838 B1 | 6/2004 | Choo et al. | |
| 6,773,911 B1 | 8/2004 | Penninger et al. | |
| 6,835,557 B1 | 12/2004 | Weissman | |
| 6,866,997 B1 | 3/2005 | Choo et al. | |
| 2002/0012909 A1 | 1/2002 | Plaksin et al. | |
| 2002/0069422 A1 | 6/2002 | Fransen | |
| 2002/0076728 A1 | 6/2002 | Maclennan et al. | |
| 2002/0192789 A1 | 12/2002 | Ley et al. | |
| 2003/0027207 A1 | 2/2003 | Filpula | |
| 2003/0040039 A1 | 2/2003 | Friedman et al. | |
| 2003/0040470 A1 | 2/2003 | Kohno | |
| 2003/0059911 A1 | 3/2003 | Yamaoka et al. | |
| 2003/0078203 A1 | 4/2003 | Paul et al. | |
| 2003/0100508 A1 | 5/2003 | Simon et al. | |
| 2003/0175799 A1 | 9/2003 | Cochran et al. | |
| 2003/0190598 A1 | 10/2003 | Tanha et al. | |
| 2004/0058318 A1 | 3/2004 | Darnell et al. | |
| 2004/0142379 A1 | 7/2004 | St. Hilaire et al. | |
| 2004/0253247 A1 | 12/2004 | Dennis et al. | |
| 2005/0079543 A1 | 4/2005 | Darnell et al. | |
| 2005/0084491 A1 | 4/2005 | Shealy et al. | |
| 2005/0100963 A1 | 5/2005 | Sato et al. | |
| 2005/0136428 A1 | 6/2005 | Crea | |
| 2005/0142558 A1 | 6/2005 | Parkar et al. | |
| 2005/0196810 A1 | 9/2005 | Cochran et al. | |
| 2005/0245454 A1 | 11/2005 | Goldstein | |
| 2005/0272093 A1 | 12/2005 | MacKinnon | |

FOREIGN PATENT DOCUMENTS

| | | |
|---|---|---|
| WO | WO 99/29337 A1 | 6/1999 |
| WO | WO 03 011892 A2 * | 7/2002 |
| WO | WO 03/020201 A2 * | 8/2002 |

OTHER PUBLICATIONS

Herman et al., 2007. The trp cage motif as a scaffold for the display of a randomized peptide library on bacteriophage T7. Journal of Biological Chemistry, 282(13): 9813-9824.*
Agu, R. U.; Valiveti, S.; Earles, D. C.; Klausner, M.; Hayden, P. J.; Wermeling, D. P.; and Stinchcomb, A. L.; "Intranasal Delivery of Recombinant Human Parathyrold Hormone [HPTH (1-34)], Teriparatide in Rats;" *Endocr. Res*; Aug. 2004; 30 (3); 455-467.
Andersen, N.H.; Barua,B.; Fesinmeyer,R.M.; Neidigh, J.; "Optimizing Aqueous Fold Stability for Short Polypeptides: 20 Residue Miniprotein Constructs That Melt as High as at 61° C., " *Peptides: The Wave of the Future*; Michal Lebl and Richard A. Houghten (Editors), American Peptide Society, 2001, p. 406.
Lane, N. E.; "Parathyroid Hormone: Evolving Therapeutic Concepts 1;" *Curr. Opin. Rheumatol.*; Jul. 2004; 16 (4); 457-463.
Neidigh, J. W.; Fesinmeyer, R. M.; and Andersen, N. H.; "Designing a 20-Residue Protein;" *Nat. Struct. Biol*; Jun. 2002; 9 (6); 425-430.

* cited by examiner

*Primary Examiner*—Mark L. Shibuya
*Assistant Examiner*—Amber D. Steele
(74) *Attorney, Agent, or Firm*—Richard R. Eckman; Nastech Pharmaceutical Company Inc.

(57) ABSTRACT

Trp cage binding domain polypeptides are disclosed. The Trp cage binding domains have the generic formulas of SEQ ID NO: 2, 7, 10 or 11. They can be efficiently produced and screened using phage display technology.

28 Claims, No Drawings

PHAGE DISPLAYED TRP CAGE LIGANDS

This claims the benefit of U.S. Provisional Application Ser. No. 60/515,533 filed on Oct. 29, 2003 the entire contents of which are incorporated herein by reference.

BACKGROUND OF THE INVENTION

The teachings of all of the references cited herein are incorporated herein by reference.

Many disease states are associated with the over-expression of a receptor such as the Her2/Neu receptor in breast cancer or an enzyme such as protein kinase in some cancer. It has been the strategy for sometime to develop small peptide antagonists to these receptors or enzymes, however, the random isolation and screening of polypeptides has been slow and produced relatively few results. Thus there is a need to provide for a rapid method for discovering peptide ligands that bind to and antagonize disease-associated receptors or ligands.

DESCRIPTION OF THE INVENTION

The present invention relates to the construction, expression, and selection of the mutated genes that encode novel Trp cage polypeptides with desirable binding properties, as well as the novel Trp cage polypeptides themselves. The substances or targets bound by these novel Trp cage polypeptides may be but need not be proteins or polypeptides. Targets may include other biological or synthetic macromolecules as well as other organic and inorganic substances. The present invention achieves genetic variants of Trp cage-encoding nucleic acids through controlled random mutagenesis of the nucleic acids yielding a mixture of Trp cage polypeptides that are capable of binding targets. It selects for novel mutated Trp cage encoding nucleic acids that encode novel Trp cage polypeptides with desirable binding properties by 1) arranging that the Trp cage polypeptide of each mutated nucleic acid be displayed on the outer surface of a microbe (a cell, spore or virus) that contains the gene, and 2) using affinity selection—selection for binding to the target material—to enrich the population of packages for those packages containing genes specifying novel Trp cage polypeptides with improved binding to that target material. Finally, enrichment is achieved by allowing only the genetic packages, which, by virtue of the displayed novel Trp cage polypeptides, bound to the target, to reproduce.

The 20 amino acid residue tryptophan cage or Trp-cage was so named because the side chain of a tryptophan residue is penned in by several other residues, notably the side-chains of prolines. The Trp-cage motif was derived from the 39 amino acid residue exendin-4 polypeptide, which is found in the venom of the Gila Monster (*Heloderma suspetum*). It was shown by NMR that the last 9 amino acid residue at the C-terminus of exendin-4 form a Trp cage. Exendin-4 has the following amino acid sequence: HGEGTFTSDLSKQMEEEAVRLFIEWLKNGGPSSGAPPS (SEQ ID NO: 1). From these observations a generic 20 amino acid residue Trp-cage polypeptide was developed having the following amino acid sequence: XFXXWXXXXGPXXXXPPPX (SEQ ID NO: 2), wherein X is any amino acid.

Thus, according to the present invention, a peptide library is produced using random nucleic acid sequences that encode up to about 10⁹ different Trp-cage peptides. A nucleic acid sequence that can be used to produce the Trp-cage amino acid sequence of SEQ ID NO: 2, for Trp-1 is:

5' CA TGT TTC GGC CGA <u>MNN AGG AGG AGG MNN MNN MNN</u>

<u>MNN AGG ACC MNN MNN MNN MNN CCA MNN MNN AAA MNN</u>

AGA GTG AGA ATA GAA AGG TAC CCG GG 3' (SEQ ID NO:3)

The underlined portion of SEQ ID NO:3 <u>MNN AGG AGG</u>

<u>AGG MNN MNN MNN MNN AGG ACC MNN MNN MNN MNN CCA MNN</u>

<u>MNN AAA MNN</u> (SEQ ID NO: 4), encodes the Trp-cage,

After cloning and expression, the Trp-cage amino acid sequence will be XFXXWXXXXGPXXXXPPPX (SEQ ID NO: 2)

The rest of the oligonucleotide allows it to bind to the extension primer and contains flanking restriction enzyme sites.

Trp-2: To get the Y-containing motif the following oligonucleotide was designed;

5' CA TGT TTC GGC CGA <u>MNN AGG AGG AGG MNN MNN MNN</u>

<u>MNN AGG ACC MNN MNN MNN MNN CCA MNN MNN ATA MNN</u>

<u>ATT</u> AGA GTG AGA ATA GAA AGG TAC CCG GG

3' (SEQ ID NO: 5)

The underlined portion <u>MNN AGG AGG AGG MNN MNN MNN</u>

<u>MNN AGG ACC MNN MNN MNN MNN CCA MNN MNN ATA MNN</u>

<u>ATT</u> (SEQ ID NO: 6) encodes the Trp-cage.

After cloning and expression, the Trp-cage amino acid sequence will be NXYXXWXXXXGPXXXXPPPX (SEQ ID NO: 7)

Trp-3: To add a terminal tri-mer of Glycine which adds freedom of movement at the point of attachment to the phage, the following oligonucleotide was designed;

(SEQ ID NO: 8)
5' CA TGT TTC GGC CGA <u>ACC ACC ACC MNN AGG AGG AGG</u>

<u>MNN MNN MNN MNN AGG ACC MNN MNN MNN MNN CCA MNN MNN</u>

<u>ATA MNN ATT</u> AGA GTG AGA ATA GAA AGG TAC CCG GG 3'

The underlined portion of the polynucleotide,
(SEQ ID NO: 9)
<u>ACC ACC ACC MNN AGG AGG AGG MNN MNN MNN MNN AGG ACC</u>

<u>MNN MNN MNN MNN CCA MNN MNN ATA MNN ATT</u> encodes the Trp-cage.

The double-underlined portion attaches the Trp-cage to the phage so as to allow freedom of movement.

After cloning and expression, the Trp-cage amino acid sequence will be NXYXXWXXXXGPXXXXPPXGGG (SEQ ID NO: 10).

Trp-4: A fourth version of the Trp-cage would be comprised of the following amino acid sequence: AAADXYXQWLXXXGPXS GRPPPX(SEQ ID NO: 11). Thus, a nucleic acid sequence encoding a polypeptide comprised of SEQ ID NO: 11 would be placed in a phage-display system. An example of a nucleic acid encoding a polypeptide that would encode the polypeptide of SEQ ID NO: 11 is:

cacatgccccgaattcggcagcagcagatnnktacnnkcagtggttannk nnknnkggtcctnnktctggtaggcctccccccnnktaacaagcttgaac atg (SEQ ID NO: 12).

In the nucleotide sequence described above, the nucleotide "M" is either an 'A', adenine or a 'C', cytosine; K is a G, guanine or a T, thymine; and 'N' is any nucleotide, 'C', cytosine, 'T' thymine, 'A', adenine, or 'G', guanine.

Using the above-described nucleic acid sequences, a plethora of Trp-cage peptides can be produced using bacteriophage (phage) display techniques. Phage-display is a technique by which non-viral polypeptides are displayed as fusion proteins on the coat protein on the surface of bacteriophage particles.

The display strategy is first perfected by modifying a nucleic acid sequence to display a stable, structured Trp cage binding domain for which a novel Trp cage polypeptide is obtainable. It is believed that a nucleic acid that encodes polypeptides of SEQ ID NO: 2, SEQ ID NO: 7, SEQ ID NO: 10 or SEQ ID NO: 11 encompasses all of the novel Trp cage polypeptides envisioned by the present invention.

Four goals guide the various variegation plans used herein, preferably: 1) a very large number (e.g. $10^9$) of variants is available, 2) a very high percentage of the possible variants actually appears in detectable amounts, 3) the frequency of appearance of the desired variants is relatively uniform, and 4) variation occurs only at a limited number of amino-acid residues, most preferably at residues having side groups directed toward a common region on the surface of the potential binding domain.

To obtain the display of a multitude of different though related potential binding domains, applicants generate a heterogeneous population of replicable microbes each of which comprises a hybrid gene including a first DNA sequence which encodes a potential Trp cage binding domain for the target of interest and a second DNA sequence which encodes a display means, such as an outer surface protein native to the microbe but not natively associated with the potential Trp cage binding domain which causes the microbe to display the corresponding chimeric protein (or a processed form thereof) on its outer surface.

Another important aspect of the invention is that each potential Trp cage binding domain remains physically associated with the particular nucleic molecule, which encodes it. Thus, once successful Trp cage binding domains are identified, one may readily recover the gene and either express additional quantities of the novel binding protein or further mutate the gene. The form that this association takes is a "replicable genetic package", a virus, cell or spore, which replicates and expresses the Trp cage binding domain-encoding gene, and transports the binding domain to its outer surface. By virtue of the present invention, novel Trp cage polypeptides are obtained that can bind specifically to targets.

In one embodiment, the invention relates to:

a) preparing a variegated population of replicable microbes, each package including a nucleic acid construct coding for an outer-surface-displayed potential binding Trp cage binding domain polypeptide, comprising (i) a structural signal directing the display of the Trp cage binding domain polypeptide on the outer surface of the package and (ii) a potential Trp cage binding domain for binding said target, where the population collectively displays a multitude of different potential binding domains having a substantially predetermined range of variation in sequence, b) causing the expression of said Trp cage binding domain polypeptide and the display of said Trp cage binding domain polypeptide on the outer surface of such packages, c) contacting the microbes with target material with an exposed combining site, so that the potential binding domains of the Trp cage binding domain polypeptides and the target material may interact, and separating microbes bearing a potential Trp cage binding domain polypeptide that succeeds in binding the target material from microbes that do not so bind, d) recovering and replicating at least one microbe bearing a successful Trp cage binding domain polypeptide, e) determining the amino acid sequence of the successful Trp cage binding domain polypeptide of a genetic package which bound to the target material, f) obtaining the nucleic acid encoding the desired Trp cage binding domain polypeptide from the microbe and placing it into a suitable expression system. (The Trp cage binding domain may then be expressed as a unitary protein, or as a domain of a larger protein).

The invention likewise encompasses the procedure by which the display strategy is verified. The microbes are engineered to display a single Trp cage binding domain polypeptide binding sequence. (Variability may be introduced into DNA subsequences adjacent to the Trp cage binding domain subsequence and within the outer surface gene so that the Trp cage binding domain polypeptide will appear on the surface of the microbe.) A molecule, such as an antibody, having high affinity for correctly folded Trp cage binding domain polypeptide is used to: a) detect a Trp cage binding domain polypeptide on the surface of the microbe, b) screen colonies for display of Trp cage binding domain polypeptide on the microbe surface, or c) select microbes that display Trp cage binding domain polypeptides from a population, some members of which might display Trp cage binding domain polypeptides on the surface of the microbe such as in one preferred embodiment, this verification process (part I) involves:

1) choosing a microbe such as a bacterial cell, bacterial spore, or phage, having a suitable outer surface protein, 2) choosing a novel Trp cage binding domain polypeptide, 3) designing an amino acid sequence that: a) includes the Trp cage binding domain as a subsequence and b) will cause the Trp cage binding domain polypeptide to appear on the surface of the genetic package, 4) engineering a vector sequence that: a) codes for the designed Trp cage binding domain amino acid sequence, b) provides the necessary genetic regulation, and c) introduces convenient sites for genetic manipulation, 5) cloning the vector sequence into the microbe, and 6) harvesting the transformed microbes and testing them for presence of the Trp cage binding domain polypeptide on the surface of the microbe; this test is performed with a target molecule having high affinity for the Trp cage binding domain polypeptide.

For each target, there are a large number of Trp cage binding domain polypeptides that may be found by the method of the present invention.

Display Strategy: Displaying Foreign Binding Domains on the Surface of a Microbe A. General Requirements It is emphasized that the microbe on which selection-through-binding will be practiced must be capable, after the selection, either of growth in some suitable environment or of in vitro amplification and recovery of the encapsulated genetic message. During at least part of the growth, the increase in number is preferably approximately exponential with respect to time. The component of a population that exhibits the desired binding properties may be quite small. Once this component of the population is separated from the non-binding components, it must be possible to amplify it. Culturing viable cells is the most powerful amplification of genetic material known and is preferred. Genetic messages can also be amplified in vitro, e.g. by PCR, but this is not the most preferred method.

Preferred microbes are vegetative bacterial cells, bacterial spores and bacterial DNA viruses. Eukaryotic cells could be used as microbes but have longer dividing times and more stringent nutritional requirements than do bacteria and it is much more difficult to produce a large number of independent transformants. They are also more fragile than bacterial cells and therefore more difficult to chromatograph without damage. Eukaryotic viruses could be used instead of bacteriophage but must be propagated in eukaryotic cells and therefore suffer from some of the amplification problems mentioned above.

Nonetheless, a strain of any living cell or virus is potentially useful if the strain can be: 1) genetically altered with reasonable facility to encode a Trp cage binding domain, 2) maintained and amplified in culture, 3) manipulated to display the Trp cage binding domain where it can interact with the target material during affinity separation, and 4) affinity separated while retaining the genetic information encoding the displayed binding domain in recoverable form. Preferably, the microbe remains viable after affinity separation.

When the microbe is a bacterial cell, or a phage that is assembled periplasmically, the display means has two components. The first component is a secretion signal, which directs the initial expression product to the inner membrane of the cell (a host cell when the package is a phage). This secretion signal is cleaved off by a signal peptidase to yield a processed, mature, Trp cage binding protein. The second component is an outer surface transport signal that directs the package to assemble the processed protein into its outer surface. Preferably, this outer surface transport signal is derived from a surface protein native to the microbe.

For example, in a preferred embodiment, the hybrid gene comprises a DNA encoding a Trp cage binding domain operably linked to a signal sequence (e.g., the signal sequences of the bacterial phoA or bla genes or the signal sequence of M13 phage geneIII) and to DNA encoding a coat protein (e.g., the M13 gene III or gene VIII proteins) of a filamentous phage (e.g., M13). The expression product is transported to the inner membrane (lipid bilayer) of the host cell, whereupon the signal peptide is cleaved off to leave a processed hybrid protein. The C-terminus of the coat protein-like component of this hybrid protein is trapped in the lipid bilayer, so that the hybrid protein does not escape into the periplasmic space. (This is typical of the wild-type coat protein.) As the single-stranded DNA of the nascent phage particle passes into the periplasmic space, it collects both wild-type coat protein and the hybrid protein from the lipid bilayer. The hybrid protein is thus packaged into the surface sheath of the filamentous phage, leaving the potential binding domain exposed on its outer surface. (Thus, the filamentous phage, not the host bacterial cell, is the "replicable microbe" in this embodiment.)

If a secretion signal is necessary for the display of the potential binding domain, in an especially preferred embodiment the bacterial cell in which the hybrid gene is expressed is of a "secretion-permissive" strain.

When the microbe is a bacterial spore, or a phage, such as the T7 SELECT® phage display system from Novagen, San Diego, Calif., whose coat is assembled intracellularly, a secretion signal directing the expression product to the inner membrane of the host bacterial cell is unnecessary. In these cases, the display means is merely the outer surface transport signal, typically a derivative of a spore or phage coat protein.

There are several methods of arranging that the Trp cage binding domain gene be expressed in such a manner that the Trp cage binding domain is displayed on the outer surface of the microbe.

The replicable genetic entity (phage or plasmid) that carries the outer surface protein-Trp cage binding domain genes (derived from the outer surface protein-Trp cage binding domain gene) through the selection-through-binding process, is referred to hereinafter as the operative cloning vector. When the operative cloning vector is a phage, it may also serve as the microbe. The choice of a microbe is dependent in part on the availability of a suitable operative cloning vector and suitable outer surface protein.

Viruses are preferred over bacterial cells and spores. The virus is preferably a DNA virus with a genome size of 2 kb to 10 kb base pairs, such as (but not limited to) the filamentous (Ff) phage M13, fd, and f1; the IncN specific phage Ike and If1; IncP-specific *Pseudomonas aeruginosa* phage Pf1 and Pf3; the T7 virus and the *Xanthomonas oryzae* phage Xf.

The species chosen as a microbe should have a well-characterized genetic system and strains defective in genetic recombination should be available. The chosen strain may need to be manipulated to prevent changes of its physiological state that would alter the number or type of proteins or other molecules on the cell surface during the affinity separation procedure.

Phages

In use of a phage one needs to know which segments of the outer surface protein interact to make the viral coat and which segments are not constrained by structural or functional roles. The size of the phage genome and the packaging mechanism are also important because the phage genome itself is the cloning vector. The outer surface protein-Trp cage binding domain gene is inserted into the phage genome; therefore: 1) the genome of the phage must allow introduction of the outer surface protein-binding domain gene either by tolerating additional genetic material or by having replaceable genetic material; 2) the virion must be capable of packaging the genome after accepting the insertion or substitution of genetic material, and 3) the display of the outer surface protein-binding domain protein on the phage surface must not disrupt virion structure sufficiently to interfere with phage propagation.

Bacteriophages are excellent choices because there is little or no enzymatic activity associated with intact mature phage, and because the genes are inactive outside a bacterial host, rendering the mature phage particles metabolically inert.

For a given bacteriophage, the preferred outer surface protein is usually one that is present on the phage surface in the largest number of copies, as this allows the greatest flexibility in varying the ratio of outer surface protein-Trp cage binding domain to wild type outer surface protein and also gives the highest likelihood of obtaining satisfactory affinity separation. Moreover, a protein present in only one or a few copies usually performs an essential function in morphogenesis or infection; mutating such a protein by addition or insertion is likely to result in reduction in viability of the microbe. Nevertheless, an outer surface protein such as M13 gIII protein may be an excellent choice as outer surface protein to cause display of the Trp cage binding domain.

The user must choose a site in the candidate outer surface protein gene for inserting a Trp cage binding domain gene fragment. The coats of most bacteriophage are highly ordered. Filamentous phage can be described by a helical lattice; isometric phage, by an icosahedral lattice. Each monomer of each major coat protein sits on a lattice point and makes defined interactions with each of its neighbors. Proteins that fit into the lattice by making some, but not all, of the normal lattice contacts are likely to destabilize the virion by: a) aborting formation of the virion, b) making the virion unstable, or c) leaving gaps in the virion so that the nucleic acid is not protected. Thus in bacteriophage, unlike the cases of bacteria and spores, it is important to retain in engineered outer surface protein-Trp cage binding domain fusion proteins those residues of the parental outer surface protein that interact with other proteins in the virion. For M13 gVIII, we retain the entire mature protein, while for M13 gIII, it might suffice to retain the last 100 residues (or even fewer). Such a truncated gIII protein would be expressed in parallel with the complete gIII protein, as gIII protein is required for phage infectivity.

An especially useful system is the phage display system produced by Dyax Corporation, Cambridge, Mass. and New England Biolabs, Beverly, Mass.

Filamentous Phage:

Compared to other bacteriophage, filamentous phage in general are attractive and M13 in particular is especially attractive because: 1) the 3D structure of the virion is known; 2) the processing of the coat protein is well understood; 3) the genome is expandable; 4) the genome is small; 5) the sequence of the genome is known; 6) the virion is physically resistant to shear, heat, cold, urea, guanidinium Cl, low pH, and high salt; 7) the phage is a sequencing vector so that sequencing is especially easy; 8) antibiotic-resistance genes have been cloned into the genome with predictable results; 9) it is easily cultured and stored, with no unusual or expensive media requirements for the infected cells; 10) it has a high burst size, each infected cell yielding 100 to 1000 M13 progeny after infection; and 11) it is easily harvested and concentrated. The filamentous phage include M13, f1, fd, If1, Ike, Xf, Pf1, and Pf3.

The entire life cycle of the filamentous phage M13, a common cloning and sequencing vector, is well understood. M13 and f1 are so closely related that we consider the properties of each relevant to both; any differentiation is for historical accuracy. The genetic structure (the complete sequence, the identity and function of the ten genes, and the order of transcription and location of the promoters) of M13 is well known as is the physical structure of the virion. Because the genome is small (6423 bp), cassette mutagenesis is practical on RF M13, as is single-stranded oligonucleotide directed mutagenesis. M13 is a plasmid and transformation system in itself, and an ideal sequencing vector. M13 can be grown on Rec.$^-$.-strains of *E. coli*. The M13 genome is expandable and M13 does not lyse cells. Because the M13 genome is extruded through the membrane and coated by a large number of identical protein molecules, it can be used as a cloning vector. Thus we can insert extra genes into M13 and they will be carried along in a stable manner.

The major coat protein is encoded by gene VIII. The 50 amino acid mature gene VIII coat protein is synthesized as a 73 amino acid precoat. The first 23 amino acids constitute a typical signal-sequence which causes the nascent polypeptide to be inserted into the inner cell membrane. Whether the precoat inserts into the membrane by itself or through the action of host secretion components, such as SecA and SecY, remains controversial, but has no effect on the operation of the present invention.

An *E. coli* signal peptidase recognizes amino acids 18, 21, and 23, and, to a lesser extent, residue 22, and cuts between residues 23 and 24 of the precoat. After removal of the signal sequence, the amino terminus of the mature coat is located on the periplasmic side of the inner membrane; the carboxy terminus is on the cytoplasmic side. About 3000 copies of the mature 50 amino acid coat protein associate side-by-side in the inner membrane.

The sequence of gene VIII is known, and the amino acid sequence can be encoded on a synthetic gene, using lacUV5 promoter and used in conjunction with the LacI$^q$ repressor. The lacUV5 promoter is induced by IPTG. Mature gene VIII protein makes up the sheath around the circular ssDNA. The 3D structure of f1 virion is known at medium resolution; the amino terminus of gene VM protein is on surface of the virion. The 2D structure of M13 coat protein is implicit in the 3D structure. Mature M13 gene VIII protein has only one domain. When the microbe is M13 the gene III and the gene VIII proteins are highly preferred as outer surface protein. The proteins from genes VI, VII, and IX may also be used.

Thus, to produce novel Trp cage binding domains of the present invention we can construct a tripartite gene comprising:

1) DNA encoding a signal sequence directing secretion of parts (2) and (3) through the inner membrane, 2) DNA encoding the mutated forms of a Trp cage binding domain sequence, and 3) DNA encoding the mature M13 gVIII protein.

This gene causes a Trp cage binding domain polypeptide to appear in active form on the surface of M13 phage.

The gene III protein is a preferred outer surface protein because it is present in many copies and because its location and orientation in the virion are known. Preferably, the Trp cage binding domain is attached to the amino terminus of the mature M13 coat protein.

Similar constructions could be made with other filamentous phage. Pf3 is a well-known filamentous phage that infects *Pseudomonas aerugenosa* cells that harbor an IncP-1 plasmid. The entire genome has been sequenced and the genetic signals involved in replication and assembly are known. The major coat protein of Pf3 is unusual in having no signal peptide to direct its secretion. Thus, to cause a Trp cage binding domain to appear on the surface of Pf3, we construct a tripartite gene comprising:

1) a signal sequence known to cause secretion in *P. aerugenosa* (preferably known to cause secretion of binding domain) fused in-frame to, 2) a gene fragment encoding the Trp cage binding domain sequence, fused in-frame to, 3) DNA encoding the mature Pf3 coat protein.

Optionally, DNA encoding a flexible linker of one to 10 amino acids is introduced between the binding domain gene fragment and the Pf3 coat-protein gene. Optionally, DNA encoding the recognition site for a specific protease, such as tissue plasminogen activator or blood clotting Factor Xa, is introduced between the binding domain gene fragment and the Pf3 coat-protein gene. Amino acids that form the recognition site for a specific protease may also serve the function of a flexible linker. This tripartite gene is introduced into Pf3 so that it does not interfere with expression of any Pf3 genes. To reduce the possibility of genetic recombination, part (3) is designed to have numerous silent mutations relative to the wild-type gene. Once the signal sequence is cleaved off, the binding domain is in the periplasm and the mature coat protein acts as an anchor and phage-assembly signal. It matters not that this fusion protein comes to rest in the lipid bilayer by a route different from the route followed by the wild-type coat protein.

The amino-acid sequence of M13 pre-coat, is:

MKKSLVLKASVAVATLVPMLSFAAEGD-DPAKAAFNSLQASATEYIGYAWAMV VVIVGA-TIGIKLFKKFTSKAS (SEQ ID NO: 13)

The best site for inserting a novel protein domain into M13 CP is after A23 because SP-I cleaves the precoat protein after A23. Trp cage binding domain polypeptides appear connected to mature M13 CP at its amino terminus. Because the amino terminus of mature M13 CP is located on the outer surface of the virion, the introduced domain will be displayed on the outside of the virion.

Another vehicle for displaying the binding domain is by expressing it as a domain of a chimeric gene containing part or all of gene III. This gene encodes one of the minor coat proteins of M13. Genes VI, VII, and IX also encode minor coat proteins. Each of these minor proteins is present in about 5 copies per virion and is related to morphogenesis or infection. In contrast, the major coat protein is present in more than 2500 copies per virion. The gene VI, VII, and IX proteins are present at the ends of the virion; these three proteins are not post-translationally processed.

The single-stranded circular phage DNA associates with about five copies of the gene III protein and is then extruded through the patch of membrane-associated coat protein in such a way that the DNA is encased in a helical sheath of protein. The DNA does not base pair (that would impose severe restrictions on the virus genome); rather the bases intercalate with each other independent of sequence.

The T7 Bacteriophage Display System

An alternative method for the production and display of Trp cage ligands is the use of a phage display system based upon the bacteriophage T7. T7 is a double-stranded DNA phage the assembly of which occurs inside *E. coli* cells and mature phage are released by cell lysis. Unlike the filamentous systems described above, the Trp cage ligands displayed on the surface of T7 do not need to be capable of secretion through the cell membrane, which is a necessary step in filamentous display. An example of such a system is the T7 SELECT® phage display system produced by Novagen, San Diego, Calif.

Bacterial Cells as Recombinant Microbes

One may choose any well-characterized bacterial strain which (1) may be grown in culture (2) may be engineered to display Trp cage binding domains on its surface, and (3) is compatible with affinity selection. Among bacterial cells, the preferred genetic packages are *Salmonella typhimurium*, *Bacillus subtilis*, *Pseudomonas aeruginosa*, *Vibrio cholerae*, *Klebsiella pneumonia*, *Neisseria gonorrhoeae*, *Neisseria meningitidis*, *Bacteroides nodosus*, *Moraxella bovis*, and especially *Escherichia coli*. The potential binding miniprotein may be expressed as an insert in a chimeric bacterial outer surface protein (outer surface protein). All bacteria exhibit proteins on their outer surfaces.

In *E. coli*, LamB is a preferred outer surface protein. As discussed below, there are a number of very good alternatives in *E. coli* and there are very good alternatives in other bacterial species. There are also methods for determining the topology of outer surface proteins so that it is possible to systematically determine where to insert a binding domain into an outer surface protein gene to obtain display of a binding domain on the surface of any bacterial species.

In view of the extensive knowledge of *E. coli*, a strain of *E. coli*, defective in recombination, is the strongest candidate.

While most bacterial proteins remain in the cytoplasm, others are transported to the periplasmic space (which lies between the plasma membrane and the cell wall of gram-negative bacteria), or are conveyed and anchored to the outer surface of the cell. Still others are exported (secreted) into the medium surrounding the cell. Those characteristics of a protein that are recognized by a cell and that cause it to be transported out of the cytoplasm and displayed on the cell surface will be termed "outer-surface transport signals".

Gram-negative bacteria have outer-membrane, that form a subset of outer surface proteins. Many outer-membrane proteins span the membrane one or more times. The signals that cause outer-membrane proteins to localize in the outer membrane are encoded in the amino acid sequence of the mature protein. Outer membrane proteins of bacteria are initially expressed in a precursor form including a so-called signal peptide. The precursor protein is transported to the inner membrane, and the signal peptide moiety is extruded into the periplasmic space. There, it is cleaved off by a "signal peptidase", and the remaining "mature" protein can now enter the periplasm. Once there, other cellular mechanisms recognize structures in the mature protein which indicate that its proper place is on the outer membrane, and transport it to that location.

It is well known that the DNA coding for the leader or signal peptide from one protein may be attached to the DNA sequence coding for another protein, protein X, to form a chimeric gene whose expression causes protein X to appear free in the periplasm. That is, the leader causes the chimeric protein to be secreted through the lipid bilayer; once in the periplasm, it is cleaved off by the signal peptidase SP-I.

The use of export-permissive bacterial strains increases the probability that a signal-sequence-fusion will direct the desired protein to the cell surface. Outer surface protein-binding domain fusion proteins need not fill a structural role in the outer membranes of Gram-negative bacteria because parts of the outer membranes are not highly ordered. For large outer surface proteins there is likely to be one or more sites at which outer surface protein can be truncated and fused to binding domain such that cells expressing the fusion will display binding domains on the cell surface. Fusions of fragments of omp genes with fragments of an x gene have led to X appearing on the outer membrane. When such fusions have been made, we can design an outer surface protein-Trp cage binding domain gene by substituting binding domain for x in the DNA sequence. Otherwise, a successful outer-membrane proteins-binding domain fusion is preferably sought by fusing fragments of the best outer-membrane protein to a Trp cage binding domain, expressing the fused gene, and testing the resultant microbes for display-of-Trp cage binding domain phenotype. We use the available data about the outer-membrane proteins to pick the point or points of fusion between omp and binding domain to maximize the likelihood that binding domain will be displayed. (spacer DNA encoding flexible linkers, made, e.g., of GLY, SER, ALA and ASN, may be placed between the outer surface protein- and binding domain-derived fragments to facilitate display.)

Alternatively, we truncate outer surface protein at several sites or in a manner that produces outer surface protein fragments of variable length and fuse the outer surface protein fragments to a Trp cage binding domain; cells expressing the fusion are screened or selected which display binding domains on the cell surface. Fragments of outer surface proteins (such as OmpA) above a certain size are incorporated into the outer membrane. An additional alternative is to include short segments of random DNA in the fusion of omp fragments to binding domain and then screen or select the resulting variegated population for members exhibiting the display-of-Trp cage binding domain phenotype.

In *E. coli*, the LamB protein is a well understood outer surface protein and can be used. The *E. coli* LamB has been expressed in functional form in *S. typhimurium, V. cholerae*, and *K. pneumonia*, so that one could display a population of Trp cage binding domains in any of these species as a fusion to *E. coli* LamB. *K. pneumonia* expresses a maltoporin similar to LamB, which could also be used. In *P. aeruginosa*, the D1 protein (a homologue of LamB) can be used.

LamB of *E. coli* is a porin for maltose and maltodextrin transport, and serves as the receptor for adsorption of bacteriophages lambda and K10. LamB is transported to the outer membrane if a functional N-terminal sequence is present; further, the first 49 amino acids of the mature sequence are required for successful transport. As with other outer surface proteins, LamB of *E. coli* is synthesized with a typical signal-sequence which is subsequently removed. Homology between parts of LamB protein and other outer membrane proteins OmpC, OmpF, and PhoE has been detected, including homology between LamB amino acids 39-49 and sequences of the other proteins. These subsequences may label the proteins for transport to the outer membrane.

The amino acid sequence of LamB is known, and a model has been developed of how it anchors itself to the outer membrane. The location of its maltose and phage binding domains are also known. Using this information, one may identify several strategies by which a Trp cage binding domain insert may be incorporated into LamB to provide a chimeric outer surface protein, which displays the Trp cage binding domain on the bacterial outer membrane.

When the Trp cage binding domain polypeptides are to be displayed by a chimeric transmembrane protein like LamB, the Trp cage binding domain could be inserted into a loop normally found on the surface of the cell. Alternatively, we may fuse a 5' segment of the outer surface protein gene to the Trp cage binding domain gene fragment; the point of fusion is picked to correspond to a surface-exposed loop of the outer surface protein and the carboxy terminal portions of the outer surface protein are omitted. In LamB, it has been found that up to 60 amino acids may be inserted with display of the foreign epitope resulting. The structural features of OmpC, OmpA, OmpF, and PhoE are so similar that one expects similar behavior from these proteins.

Other bacterial outer surface proteins, such as OmpA, OmpC, OmpF, PhoE, and pilin, may be used in place of LamB and its homologues. OmpA is of particular interest because it is very abundant and because homologues are known in a wide variety of gram-negative bacterial species. Insertion of a Trp cage binding domain encoding fragment at about codon 111 or at about codon 152 is likely to cause the binding domain to be displayed on the cell surface.

Porin Protein F of *Pseudomonas aeruginosa* has been cloned and has sequence homology to OmpA of *E. coli*. The insertion of a Trp cage binding domain gene fragment at about codon 164 or at about codon 250 of the *E. coli* ompC gene or at corresponding codons of the *S. typhimurium* ompC gene is likely to cause the Trp cage binding domain to appear on the cell surface. The ompC genes of other bacterial species may be used.

OmpF of *E. coli* is a very abundant outer surface protein, .gtoreq. 104 copies/cell. Fusion of a Trp cage binding domain gene fragment, either as an insert or to replace the 3' part of ompF, in one of the indicated regions is likely to produce a functional ompF::Trp cage binding domain gene the expression of which leads to display of the Trp cage binding domain on the cell surface. In particular, fusion at about codon 111, 177, 217, or 245 should lead to a functional ompF::Trp cage binding domain gene.

Pilus proteins are of particular interest because piliated cells express many copies of these proteins and because several species (*N. gonorrhoeae, P. aeruginosa, Moraxella bovis, Bacteroides nodosus*, and *E. coli*) express related pilins. A GLY-GLY linker between the last pilin residue and the first residue of the foreign epitope to provide a "flexible linker" is very useful. Thus a preferred place to attach a Trp cage binding domain is the carboxy terminus. The exposed loops of the bundle could also be used.

The protein IA of *N. gonorrhoeae* can also be used; the amino terminus is exposed; thus, one could attach a Trp cage binding domain at or near the amino terminus of the mature P.IA as a means to display the binding domain on the *N. gonorrhoeae* surface.

The PhoE of *E. coli* has also been used. This model predicts eight loops that are exposed; insertion of a Trp cage binding domain into one of these loops is likely to lead to display of the binding domain on the surface of the cell. Residues 158, 201, 238, and 275 are preferred locations for insertion of and binding domain.

Other outer surface proteins that could be used include *E. coli* BtuB, FepA, FhuA, IutA, FecA, and FhuE, which are receptors for nutrients usually found in low abundance.

Bacterial Spores as Recombinant Microbes:

Bacterial spores have desirable properties as recombinant microbe candidates. Spores are much more resistant than vegetative bacterial cells or phage to chemical and physical agents, and hence permit the use of a great variety of affinity selection conditions. Also, *Bacillus* spores neither actively metabolize nor alter the proteins on their surface. Spores have the disadvantage that the molecular mechanisms that trigger sporulation are less well worked out than is the formation of M13 or the export of protein to the outer membrane of *E. coli*.

Bacteria of the genus *Bacillus* form end outer surface protein spores that are extremely resistant to damage by heat, radiation, desiccation, and toxic chemicals. This phenomenon is attributed to extensive intermolecular cross linking of the coat proteins. End outer surface protein spores from the genus *Bacillus* are more stable than are outer surface protein spores from *Streptomyces*. *Bacillus subtilis* forms spores in 4 to 6 hours, but *Streptomyces* species may require days or weeks to sporulate. In addition, genetic knowledge and manipulation is much more developed for *B. subtilis* than for other spore-forming bacteria. Thus *Bacillus* spores are preferred over *Streptomyces* spores. Bacteria of the genus *Clostridium* also form very durable endospores, but clostridia, being strict anaerobes, are not convenient to culture.

Viable spores that differ only slightly from wild-type are produced in *B. subtilis* even if any one of four coat proteins is missing. Moreover, plasmid DNA is commonly included in spores, and plasmid encoded proteins have been observed on the surface of *Bacillus* spores. For these reasons, we expect that it will be possible to express during sporulation a gene encoding a chimeric coat protein, without interfering materially with spore formation.

Fusions of binding domain fragments to cotC or cotD fragments are likely to cause binding domain to appear on the spore surface. The genes cotC and cotD are preferred outer surface protein genes because CotC and CotD are not post-translationally cleaved. Subsequences from cotA or cotB could also be used to cause an binding domain to appear on the surface of *B. subtilis* spores, but we must take the post-translational cleavage of these proteins into account. DNA encoding Trp cage binding domain could be fused to a fragment of cotA or cotB at either end of the coding region or at sites interior to the coding region. Spores could then be screened or selected for the display-of-binding domain phenotype.

As stated above, in the preferred embodiment of the present invention the microbe for producing the Trp cage library is a bacteriophage. The present invention is also directed towards a method for producing novel Trp cage peptide ligands comprised producing a random set of nucleic acids that encode Trp-cage peptide into a phage-display viral vector, growing the resultant virus into bacteria to produce new viruses, analyzing the resultant Trp-cage peptides expressed on the surface of the bacterially-produced viruses to find one that binds to a predetermined receptor or enzyme. The present invention also provides for substrate peptides that complex with enzymes so as to antagonize the interaction of the enzyme with its substrate.

According to the present invention, novel Trp-cage polypeptides are produced by first synthesizing the above-described polynucleotides of SEQ ID NOs: 2, 3, 5 and 8 preferably using a DNA synthesizer such as the EXPEDITE 8900®, PerSeptive Biosystems. At the steps where a nucleotide 'M' is designated, both 'A' and 'C' nucleotides are added preferably in equimolar amounts. At the steps where a nucleotide 'N' is designated, 'A', 'C', 'T' and 'G' nucleotides are added preferably in equimolar amounts. Thus results in are large number of DNA sequences being produced, which are capable of encoding upwards to $10^9$ 20 residue Trp-cage peptide sequences.

The DNA sequences, encoding the novel Trp-cage peptides are then spliced into the phages existing gene 3 sequence, and are expressed on one end of the outer protein coat of the phage. Each phage only receives one DNA, so each expresses a single Trp-cage peptide. Collectively, the population of phage can display a billion or more Trp-cage peptides. This produces a Trp-cage peptide library, which is a collection of phage displaying a population of related but diverse Trp-cage peptides. Next this library of Trp-cage peptides is exposed to receptor or enzymatic targets, which are preferably immobilized. After the phage expressing the Trp-cage peptides are given a sufficient time to bind to the potential targets, the immobilized target is washed to remove phage that did not bind to the target. One only need capture one phage that binds to the target by means of an expressed Trp-cage peptide. Several million of the positive phage can then be produced overnight providing for enough sequence for DNA sequence determination, thus identifying the amino sequence of the Trp-cage peptide and the DNA that encodes it. The Trp-cage peptides that are created and isolated using the phage display method have a specific interaction with a known disease target, making this a rapid, effective and focused drug discovery method.

Display Strategy: Displaying Trp Cage Ligands on Bacteriophage T7

An alternative method for the production and display of Trp cage ligands is the use of a phage display system based upon the bacteriophage T7. T7 is a double-stranded DNA phage the assembly of which occurs inside *E. coli* cells and mature phage are released by cell lysis. Unlike the filamentous systems described above, the Trp cage ligands displayed on the surface of T7 do not need to be capable of secretion through the cell membrane, which is a necessary step in filamentous display.

EXAMPLE 1

Methods for Insertion of the Trp Cage Library into a T7 Vector

1. The following oligonucleotide was synthesized and PAGE purified:

```
5' -CATGTTCAAGCTTGTTAMNNGGGGGGAGGACGACCAGAMNNAGGAC

CMNNMNNMNNTAACCACTGMNNGTAMNNATCTGCTGCTGCCGAATTCGG

GGCATGTG-3' (SEQ ID NO: 14)
```

The underlined bases represent positions that were varied where N=any base used in equal proportions and M=A or C (in equal portions).

2. A primer for DNA extension was also synthesized and PAGE purified by Retrogen: 5'-CACATGCCCCGAATTCGGCA-3' (SEQ ID NO: 15).
3. The primer was annealed to 10 mcg of oligo in a molar ratio of 2.6:1 by heating to 95° C. for 5 minutes in annealing buffer (10 nM Tris pH7.5, 100 mM NaCl, 1 mM EDTA) and then allowing it to come to room temperature for 1 hour.
4. The oligo with annealed primer was converted to double stranded DNA by Klenow extension at 37 C for 10 minutes and stopped by heating to 65 C for 15 minutes. The extended oligo was extracted with phenol/chloroform and ethanol precipitated.
5. The extended oligo was digested at 37° C. for 3 hours with EcoRI and HindIII using 10× EcoRI reaction buffer provided by the enzyme supplier (New England Biolabs). The reaction was stopped by heating to 65 C for 20 minutes.
6. The digestion products were separated by PAGE and a gel fragment containing the desired fragment was excised and the DNA eluted by overnight shaking in 100 mM sodium acetate pH 4.5, 1 mM EDTA, 0.1% SDS. The eluted DNA was extracted by phenol/chloroform and precipitated with ethanol to obtain a population of Trp cage library inserts as represented below:

EcoRI

```
5' -AATTCGGCAGCAGCAGATNNKTACNNKCAGTGGTTANNKNNKLNNK
3'  GCCGTCGTCGTCTANNMATGNNMGTCACCAATNMNMNMNNM

HindIII
    GGTCCTNNKTCTGGTAGGCCTCCCCCCNNKTAACA-3'

(SEQ ID NO: 16)

CCAGGANNMAGACCATCCGGAGGGGGGNNMATTGTTCGA 5'
```

7. Arms of the phage vector T7Select 10-3b pre-digested with EcoRI and HindIII were purchased from Novagen, Inc. (Note: This vector is designed to provide a valency of 5-15, but other vectors can be used to alter the valency, e.g., T7Select 1-1b)

8. T7Select 10-3b arms were ligated to the purified EcoRI/HindIII Trp cage library inserts using a T4 DNA ligation kit (Novagen, Inc.).

9. Ligated molecules were packaged into T7 capsids in vitro using T7 Packaging Extract (Novagen, Inc.) according to the supplier's instructions and infected into *E. coli* BLT 5403 (Novagen, Inc.) for phage recovery.

10. Inserts were confirmed by PCR and DNA sequencing.

The teachings of all of the references cited herein are incorporated in their entirety herein by reference.

---

What is claimed is:

1. An isolated polypeptide comprising the amino acid sequence SEQ ID NO: 11, wherein said polypeptide comprises a tryptophan cage domain.

2. The polypeptide of claim 1, wherein said polypeptide consists of 23 amino acids.

3. The polypeptide of claim 1, wherein said polypeptide further comprises in operable combination:
a first amino acid sequence directing the display of the polypeptide on the surface of a lytic phage; and optionally
a second amino acid sequence that targets the polypeptide to the inner membrane of a cell.

4. The polypeptide of claim 3, wherein the first amino acid sequence is a lytic phage coat protein or fragment thereof.

5. The polypeptide of claim 1, wherein said polypeptide is displayed on the surface of a lytic bacteriophage.

6. The polypeptide of claim 5, wherein the bacteriophage is T7.

7. The polypeptide of claim 1, wherein said polypeptide is folded into a Trp cage domain conformation.

8. An isolated polypeptide comprising the amino acid sequence SEQ ID NO: 11, wherein said polypeptide is produced from a nucleic acid comprising the sequence SEQ ID NO: 12; wherein K is guanine or thymine, and N is any nucleotide.

9. The polypeptide of claim 8, wherein K is guanine.

10. The polypeptide of claim 8, wherein said polypeptide is propagated in a bacterium via lytic bacteriophage.

11. The polypeptide of claim 10, wherein the bacterium is *Escherichia coli*.

12. A fusion protein consisting of (a) the Trp-cage binding domain SEQ ID NO:11 and (b) a carboxy terminal carrier protein moiety of a viral protein of a lytic phage, said fusion protein optionally including (c) a flexible linker between said amino and carboxy terminal moieties, said carrier protein moiety acting, when the fusion protein is produced in a host cell infected by the lytic phage, to cause the display of the fusion protein or a processed form thereof on the surface of lytic phage particles.

13. The fusion protein of claim 12 wherein the carboxy terminal moiety is a portion of a T7 bacteriophage protein.

14. The fusion protein of claim 12 wherein the carrier protein moiety corresponds to a 10-b T7 viral protein of T7.

15. A fusion protein comprising (a) a carrier protein moiety corresponding to a 10-b protein of a T7 phage, said carrier protein moiety acting, when the fusion protein is produced in a host cell infected by T7 phage, to cause the display of the fusion protein or a processed form thereof on the surface of the phage, and (b) a Trp cage binding domain attached to the amino terminus of said carrier protein moiety, wherein the Trp cage binding domain is a polypeptide comprising the amino acid sequence SEQ ID NO: 11.

16. A lytic phage particle bearing a fusion protein according to claim 12.

17. A library of lytic phage comprising Trp cage fusion protein-bearing phage according to claim 16 collectively displaying a plurality of Trp cage binding domains.

18. A lytic phage bearing on its outer surface a chimeric Trp cage binding protein, said protein comprising (i) the Trp cage binding domain SEQ ID NO: 11, and at least a functional portion of a coat protein of said phage, said portion acting, when the chimeric protein is produced in a suitable host cell, to cause the display of the chimeric Trp cage binding protein or a processed form thereof on the outer surface of the phage.

19. The lytic phage of claim 18 wherein the phage is a T7 phage.

20. The lytic phage of claim 18 wherein the coat protein is a T7 phage protein.

21. The lytic phage of claim 20 wherein the coat protein is the T7 10-b protein.

22. The lytic phage of claim 18 wherein the chimeric protein further comprises a flexible linker, linking said Trp cage binding domain to said portion of coat protein, which is specifically cleavable by a site-specific protease.

23. The lytic phage of claim 22 wherein the site-specific protease is Factor Xa, Factor XIa, Kallikvein, thrombin, Factor XIIa, collagenase or enterokinase.

24. The lytic phage of claim 18, said phage further bearing on its outer surface the corresponding wild-type coat protein of said phage.

25. The lytic phage of claim 18 wherein the Trp cage binding domain is coupled to the amino terminus of the processed coat protein.

26. A library of lytic phage displaying Trp cage binding domains comprising the amino acid sequence SEQ ID NO: 11.

27. A method for obtaining a nucleic acid encoding a Trp cage binding domain comprising:

a) preparing a variegated population of lytic phage, each phage including a nucleic acid construct coding for a chimeric Trp cage binding protein, each said construct comprising DNA encoding (i) a Trp cage binding domain of the amino acid sequence SEQ ID NO: 11, and (ii) an outer surface transport signal for obtaining the display of the Trp cage binding domain on the outer surface of the phage, wherein said variegated population of phage collectively display a plurality of different Trp cage binding domains, the differentiation among said plurality of different Trp cage binding domains occurring through the random variation of one or more of the seven Xaa amino acid positions of SEQ ID NO: 11;

b) causing the expression of said chimeric Trp cage binding proteins and the display of said Trp cage binding domains on the outer surfaces of said phage;

c) contacting said population of phage with a target material such that said Trp cage binding domains and the target material interact;

d) separating phage displaying a Trp cage binding domain that binds the target material from phage that do not so bind, and e) recovering at least one phage displaying on its outer surface a chimeric Trp cage binding protein comprising a Trp cage binding domain, said phage enclosing said DNA encoding the Trp cage binding domain.

28. The method of claim 27 wherein said phage are amplifiable in cell culture.

* * * * *

SEQUENCE LISTING

```
<160> NUMBER OF SEQ ID NOS: 17

<210> SEQ ID NO 1
<211> LENGTH: 38
<212> TYPE: PRT
<213> ORGANISM: Heloderma suspetum

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 2
<211> LENGTH: 19
<212> TYPE: PRT
<213> ORGANISM: Heloderma suspetum
<220> FEATURE:
<221> NAME/KEY: VARIANT
<222> LOCATION: 1, 3, 4, 6, 7, 8, 9, 12, 13, 14, 15, 19
<223> OTHER INFORMATION: Xaa = Any Amino Acid

<400> SEQUENCE: 2

Xaa Phe Xaa Xaa Trp Xaa Xaa Xaa Xaa Gly Pro Xaa Xaa Xaa Xaa Pro
1               5                   10                  15

Pro Pro Xaa

<210> SEQ ID NO 3
<211> LENGTH: 97
<212> TYPE: DNA
<213> ORGANISM: Heloderma suspetum
<220> FEATURE:
<221> NAME/KEY: misc_feature
<222> LOCATION: 15, 27, 30, 33, 36, 45, 48, 51, 54, 60, 63, 69
<223> OTHER INFORMATION:
      m = A or C
<220> FEATURE:
<221> NAME/KEY: misc_feature
<222> LOCATION: 16, 17, 28, 29, 31, 32, 34, 35, 37, 38, 46, 47, 49, 50,
      52, 53, 55, 56, 61, 62, 64, 65, 70, 71
<223> OTHER INFORMATION: n = A,T,C or G

<400> SEQUENCE: 3
catgtttcgg ccgamnnagg aggaggmnnm nnmnnmnnag gaccmnnmnn mnnmnnccam    60
nnmnnaaamn nagagtgaga atagaaaggt acccggg                            97
```

```
<210> SEQ ID NO 4
<211> LENGTH: 57
<212> TYPE: DNA
<213> ORGANISM: Heloderma suspetum
<220> FEATURE:
<221> NAME/KEY: misc_feature
<222> LOCATION: 1, 13, 16, 19, 22, 31, 34, 37, 40, 46, 49, 55
<223> OTHER INFORMATION:
    m = A or C
<220> FEATURE:
<221> NAME/KEY: misc_feature
<222> LOCATION: 2, 3, 14, 15, 17, 18, 20, 21, 23, 24, 32, 33, 35, 36,
    38, 39, 41, 42, 47, 48, 50, 51, 56, 57
<223> OTHER INFORMATION: n = A,T,C or G

<400> SEQUENCE: 4
mnnaggagga ggmnnmnnmn nmnnaggacc mnnmnnmnnm nnccamnnmn naaamnn          57

<210> SEQ ID NO 5
<211> LENGTH: 100
<212> TYPE: DNA
<213> ORGANISM: Heloderma suspetum
<220> FEATURE:
<221> NAME/KEY: misc_feature
<222> LOCATION: 15, 27, 30, 33, 36, 45, 48, 51, 54, 60, 63, 69
<223> OTHER INFORMATION:
    m = A or C
<220> FEATURE:
<221> NAME/KEY: misc_feature
<222> LOCATION: 16, 17, 28, 29, 31, 32, 34, 35, 37, 38, 46, 47, 49, 50,
    52, 53, 55, 56, 61, 62, 64, 65, 70, 71
<223> OTHER INFORMATION: n = A,T,C or G

<400> SEQUENCE: 5
catgtttcgg ccgamnnagg aggaggmnnm nmnnmnnag gaccmnnmnn mnnmnnccam          60
nnmnnatamn nattagagtg agaatagaaa ggtacccggg                             100

<210> SEQ ID NO 6
<211> LENGTH: 60
<212> TYPE: DNA
<213> ORGANISM: Heloderma suspetum
<220> FEATURE:
<221> NAME/KEY: misc_feature
<222> LOCATION: 1, 13, 16, 19, 22, 31, 34, 37, 40, 46, 49, 55
<223> OTHER INFORMATION:
    m = A or C
<220> FEATURE:
<221> NAME/KEY: misc_feature
<222> LOCATION: 2, 3, 14, 15, 17, 18, 20, 21, 23, 24, 32, 33, 35, 36,
    38, 39, 41, 42, 47, 48, 50, 51, 56, 57
<223> OTHER INFORMATION: n = A,T,C or G

<400> SEQUENCE: 6
mnnaggagga ggmnnmnnmn nmnnaggacc mnnmnnmnnm nnccamnnmn natamnnatt         60

<210> SEQ ID NO 7
<211> LENGTH: 20
<212> TYPE: PRT
<213> ORGANISM: Heloderma suspetum
<220> FEATURE:
<221> NAME/KEY: VARIANT
<222> LOCATION: 2, 4, 5, 7, 8, 9, 10, 13, 14, 15, 16, 20
<223> OTHER INFORMATION: Xaa = Any Amino Acid

<400> SEQUENCE: 7

Asn Xaa Tyr Xaa Xaa Trp Xaa Xaa Xaa Xaa Gly Pro Xaa Xaa Xaa Xaa
 1               5                  10                  15

Pro Pro Pro Xaa
```

-continued

<210> SEQ ID NO 8
<211> LENGTH: 109
<212> TYPE: DNA
<213> ORGANISM: Heloderma suspetum
<220> FEATURE:
<221> NAME/KEY: misc_feature
<222> LOCATION: 24, 36, 39, 42, 45, 54, 57, 60, 63, 69, 72, 78
<223> OTHER INFORMATION:
    m = A or C
<220> FEATURE:
<221> NAME/KEY: misc_feature
<222> LOCATION: 25, 26, 37, 38, 40, 41, 43, 44, 46, 47, 55, 56, 58, 59,
    61, 62, 64, 65, 70, 71, 73, 74, 79, 80
<223> OTHER INFORMATION: n = A,T,C or G

<400> SEQUENCE: 8
catgtttcgg ccgaaccacc accmnnagga ggaggmnnmn nmnnmnnagg accmnnmnnm      60
nnmnnccamn nmnnatamnn attagagtga gaatagaaag gtacccggg                 109

<210> SEQ ID NO 9
<211> LENGTH: 69
<212> TYPE: DNA
<213> ORGANISM: Heloderma suspetum
<220> FEATURE:
<221> NAME/KEY: misc_feature
<222> LOCATION: 10, 22, 25, 28, 31, 40, 43, 46, 49, 55, 58,
<223> OTHER INFORMATION:
    m = A or C
<220> FEATURE:
<221> NAME/KEY: misc_feature
<222> LOCATION: 11, 12, 23, 24, 26, 27, 29, 30, 32, 33, 41, 42, 44, 45,
    47, 48, 50, 51, 56, 57, 59, 60, 65, 66
<223> OTHER INFORMATION: n = A,T,C or G

<400> SEQUENCE: 9
accaccaccm nnaggaggag gmnnmnnmn mnnaggaccm nnmnnmnnmn nccamnnmnn      60 atamnnatt                                                              69

<210> SEQ ID NO 10
<211> LENGTH: 23
<212> TYPE: PRT
<213> ORGANISM: Heloderma suspetum
<220> FEATURE:
<221> NAME/KEY: VARIANT
<222> LOCATION: 2, 4, 5, 7, 8, 9, 10, 13, 14, 15, 16, 20
<223> OTHER INFORMATION: Xaa = Any Amino Acid

<400> SEQUENCE: 10

Asn Xaa Tyr Xaa Xaa Trp Xaa Xaa Xaa Xaa Gly Pro Xaa Xaa Xaa Xaa
 1               5                  10                  15

Pro Pro Pro Xaa Gly Gly Gly
            20

<210> SEQ ID NO 11
<211> LENGTH: 23
<212> TYPE: PRT
<213> ORGANISM: Heloderma suspetum
<220> FEATURE:
<221> NAME/KEY: VARIANT
<222> LOCATION: 5, 7, 11, 12, 13, 16, 23
<223> OTHER INFORMATION: Xaa = Any Amino Acid

<400> SEQUENCE: 11

Ala Ala Ala Asp Xaa Tyr Xaa Gln Trp Leu Xaa Xaa Xaa Gly Pro Xaa
 1               5                  10                  15

Ser Gly Arg Pro Pro Xaa
            20

<210> SEQ ID NO 12
<211> LENGTH: 103
<212> TYPE: DNA
<213> ORGANISM: Heloderma suspetum
<220> FEATURE:
<221> NAME/KEY: misc_feature
<222> LOCATION: 32, 38, 50, 53, 56, 65, 86
<223> OTHER INFORMATION: k = G or T
<220> FEATURE:
<221> NAME/KEY: misc_feature
<222> LOCATION: 30, 31, 36, 37, 48, 49, 51, 52, 54, 55, 63, 64, 84, 85
<223> OTHER INFORMATION: n = A,T,C or G

<400> SEQUENCE: 12
cacatgcccc gaattcggca gcagcagatn nktacnnkca gtggttannk nnknnkggtc    60
ctnnktctgg taggcctccc cccnnktaac aagcttgaac atg                     103

<210> SEQ ID NO 13
<211> LENGTH: 73
<212> TYPE: PRT
<213> ORGANISM: E. coli

<400> SEQUENCE: 13

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30

Ala Phe Asn Ser Leu Gln Ala Ser Ala Thr Glu Tyr Ile Gly Tyr Ala
        35                  40                  45

Trp Ala Met Val Val Val Ile Val Gly Ala Thr Ile Gly Ile Lys Leu
    50                  55                  60

Phe Lys Lys Phe Thr Ser Lys Ala Ser
65                  70

<210> SEQ ID NO 14
<211> LENGTH: 103
<212> TYPE: DNA
<213> ORGANISM: Heloderma suspetum
<220> FEATURE:
<221> NAME/KEY: misc_feature
<222> LOCATION: 18, 39, 48, 51, 54, 66, 72
<223> OTHER INFORMATION:
    m = A or C
<220> FEATURE:
<221> NAME/KEY: misc_feature
<222> LOCATION: 19, 20, 40, 41, 49, 50, 52, 53, 55, 56, 67, 68, 73, 74
<223> OTHER INFORMATION: n = A,T,C or G

<400> SEQUENCE: 14
catgttcaag cttgttamnn gggggagga cgaccagamn naggaccmnn mnnmnntaac    60
cactgmnngt amnnatctgc tgctgccgaa ttcggggcat gtg                     103

<210> SEQ ID NO 15
<211> LENGTH: 20
<212> TYPE: DNA
<213> ORGANISM: Heloderma suspetum

<400> SEQUENCE: 15
cacatgcccc gaattcggca                                               20

<210> SEQ ID NO 16

-continued

```
<211> LENGTH: 80
<212> TYPE: DNA
<213> ORGANISM: Heloderma suspetum
<220> FEATURE:
<221> NAME/KEY: misc_feature
<222> LOCATION: 21, 27, 39, 42, 45, 54, 75
<223> OTHER INFORMATION:
      k = G or T
<220> FEATURE:
<221> NAME/KEY: misc_feature
<222> LOCATION: 19, 20, 25, 26, 37, 38, 40, 41, 43, 44, 52, 53, 73, 74
<223> OTHER INFORMATION: n = A,T,C or G

<400> SEQUENCE: 16
aattcggcag cagcagatnn ktacnnkcag tggttannkn nknnkggtcc tnnktctggt      60
aggcctcccc ccnnktaaca                                                 80

<210> SEQ ID NO 17
<211> LENGTH: 77
<212> TYPE: DNA
<213> ORGANISM: Heloderma suspetum
<220> FEATURE:
<221> NAME/KEY: misc_feature
<222> LOCATION: 10, 31, 40, 43, 55, 61
<223> OTHER INFORMATION:
      m = A or C
<220> FEATURE:
<221> NAME/KEY: misc_feature
<222> LOCATION: 11, 12, 32, 33, 41, 42, 44, 45, 56, 57, 62, 63
<223> OTHER INFORMATION: n = A,T,C or G

<400> SEQUENCE: 17
agcttgttam nnggggggag gcctaccaga mnnaggaccm nnmnntaacc actgmnngta      60
mnnatctgct gctgccg                                                    77
```